(12) United States Patent
Matsumoto et al.

(10) Patent No.: US 7,504,370 B2
(45) Date of Patent: Mar. 17, 2009

(54) DETERGENT COMPOSITION

(75) Inventors: Chikako Matsumoto, Wakayama (JP); Nobuaki Tatsuta, Wakayama (JP); Morinobu Fukuda, Tokyo (JP); Tetsuya Miyajima, Wakayama (JP); Kennichi Kasuga, Tokyo (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 10/969,842

(22) Filed: Oct. 22, 2004

(65) Prior Publication Data

US 2005/0113281 A1    May 26, 2005

Related U.S. Application Data

(63) Continuation of application No. 10/088,500, filed as application No. PCT/JP00/07044 on Oct. 11, 2000.

(30) Foreign Application Priority Data

Oct. 12, 1999 (JP) ................... 11-289880

(51) Int. Cl.
*C11D 1/00* (2006.01)
*C11D 3/20* (2006.01)
*C11D 3/36* (2006.01)
*C11D 3/44* (2006.01)

(52) U.S. Cl. ............... 510/137; 510/119; 510/130; 510/138; 510/467; 510/506; 424/70.23

(58) Field of Classification Search ............... 510/119, 510/130, 137, 138, 467, 506; 424/70.23
See application file for complete search history.

(56) References Cited

U.S. PATENT DOCUMENTS 2,900,346 A   8/1959  Fowkes et al.
5,015,471 A * 5/1991  Birtwistle et al. ......... 424/70.19
5,753,608 A   5/1998  Zack et al.
6,855,677 B1 * 2/2005  Matsumoto et al. ......... 510/122

FOREIGN PATENT DOCUMENTS

| | | |
|---|---|---|
| EP | 0 245 756 | 11/1987 |
| EP | 474023 | 3/1992 |
| EP | 0 496 359 | 7/1992 |
| EP | 0 671 463 | 9/1995 |
| JP | 3-153796 | 7/1991 |
| JP | 5-125086 | 5/1993 |
| JP | 6-212190 | 8/1994 |
| JP | 8-165235 | 6/1996 |
| WO | WO01/10991 | 2/2001 |

* cited by examiner

*Primary Examiner*—Gregory R Del Cotto
(74) *Attorney, Agent, or Firm*—Oblon, Spivak, McClelland, Maier & Neustadt, P.C.

(57) ABSTRACT

Detergent compositions each of which comprises (A) at least one phosphate ester or a salt thereof represented by the following formula (1):

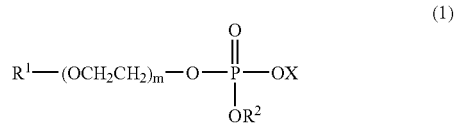

wherein $R^1$ represents a $C_8$-$C_{18}$ hydrocarbon group, m stands for a number of from 0 to 10 on weight average, X represents H, an alkali metal atom, ammonium, a basic amino acid residual group, or an alkanolamino group having a hydroxy ($C_2$-$C_3$ alkyl) group, and $R^2$ represents $-(CH_2CH_2O)_m-R^1$ or X, or a mixture thereof, and (B) at least one glyceryl ether having a $C_4$-$C_{12}$ alkyl or alkenyl group.

These detergent compositions are low in skin irritation and are good in foaming performance.

18 Claims, No Drawings

US 7,504,370 B2

DETERGENT COMPOSITION

This application is a continuation application of U.S. patent application Ser. No. 10/088,500, filed Jul. 9, 2002; which is a National Stage Application of International Application No. PCT/JP00/07044, filed on Oct. 11, 2000.

TECHNICAL FIELD

This invention relates to detergent compositions, which are low in skin irritation and are good in foamability.

BACKGROUND ART

Detergent compositions which are brought into direct contact with skin, such as shampoos and body washes, are required to provide low irritation to the skin in addition to high detergency, good foaming performance and good sensation upon application. Sulfate salt type surfactants widely employed as detergent components may irritate the eyes upon shampooing, or when used over an extended period of time, those having sensitive skin may tend to have roughened hands or skin, although these surfactants are high in foaming performance. Further, detergent compositions containing so-called low-irritation surfactants such as acetate salt type surfactants, amphoteric surfactants or surfactants having saccharide skeletons as principal components lead to inferior cleansing effect and foamability, thereby making it difficult to obtain fully satisfactory detergents.

Phosphate ester type surfactants, on the other hand, have a problem in that they are inferior in foamability, although they are satisfactory in reduced irritation to skin and also in detergency.

U.S. Pat. No. 2,900,346 discloses a foaming detergent comprising an organic sulfate salt or sulfonate salt surfactant together with a glycerol monoalkyl ether. In this patent, however, the glyceryl monoalkyl ether is described as being effective for the stabilization of foam, and is used as a foam stabilizer. Further, a detergent added with an organic sulfate salt or sulfonate salt surfactant is irritant to skin and is not preferred.

An object of the present invention is, therefore, to provide a detergent composition which provides reduced irritation to skin and has a good foamability.

DISCLOSURE OF THE INVENTION

The present inventors have found that a glyceryl ether of a specific structure has an effect to increase foamability of a particular phosphate ester type surfactant and that their combined use makes it possible to obtain a detergent composition which provides low irritation to skin and good foam.

The present invention provides a detergent composition comprising:
(A) at least one phosphate ester or a salt thereof represented by the following formula (1):

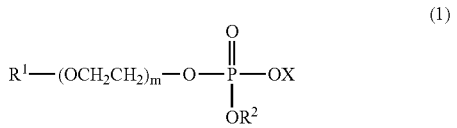

wherein $R^1$ represents a linear or branched hydrocarbon group having 8 to 18 carbon atoms, m stands for a number of from 0 to 10 on weight average, X represents a hydrogen atom, an alkali metal atom, ammonium, a basic amino acid residual group, or an alkanolamino group having a hydroxyalkyl group of 2 or 3 carbon atoms, and $R^2$ represents $-(CH_2CH_2O)_m-R^1$ or X; or a mixture thereof, and
(B) at least one glyceryl ether having an alkyl or alkenyl group of 4 to 12 carbon atoms.

The present invention also provides a method for enhancing foamability in a detergent composition comprising the component (A), which comprises adding thereto the component (B).

BEST MODES FOR CARRYING OUT THE INVENTION

The phosphate ester useful as the component (A) in the present invention is a mono- or di-ester of phosphoric acid, which is represented by the formula (1). $R^1$ in the formula (1) is a linear or branched hydrocarbon having 8 to 18 carbon atoms. The carbon number is preferably from 8 to 16, and particularly preferably from 8 to 15.

Examples of the linear hydrocarbon group as $R^1$, which has 8 to 18 carbon atoms, include alkyl groups and alkenyl groups having 8 to 18 carbon atoms, preferably linear $C_8$-$C_{16}$ alkyl groups such as octyl, nonyl, decyl, undecyl, dodecyl, tridecyl, tetradecyl and pentadecyl, with linear $C_8$-$C_{15}$ alkyl group being particularly preferred.

On the other hand, examples of the branched hydrocarbon group as $R^1$, which has 8 to 18 carbon atoms, include methyl-branched hydrocarbon groups represented by $R^3$—CH(CH$_3$)CH$_2$— ($R^3$ represents a linear hydrocarbon group having 5 to 12 carbon atoms), with methyl-branched alkyl groups being particularly preferred. Illustratives of the linear hydrocarbon group having 5 to 12 carbon atoms represented by $R^3$ are linear alkyl or alkenyl groups having 5 to 12 carbon atoms, with linear alkyl groups such as pentyl, hexyl, heptyl, octyl, nonyl, decyl, undecyl and dodecyl being particularly preferred. In addition to these methyl-branched alkyl groups, α-branched alkyl groups such as ethyl-branched, propyl-branched, butyl-branched and pentyl-branched alkyl groups can also be used.

In the formula (1), m is preferably from 0 to 5 on weight average. More preferably, m ranges from 0 to 3, with 0 being especially preferred.

$R^2$ is $-(CH_2CH_2O)_m-R^1$ or X, in which $R^1$, m and X have the same meanings as defined above. Preferred as $R^2$ is $-(CH_2CH_2O)_m-R^1$, in which m is from 0 to 5 and $R^1$ is the above-mentioned preferred group or a hydrogen atom.

Examples of the alkali metal as X include lithium, sodium, potassium and the like; examples of the basic amino acid for the basic amino acid residual group as X include arginine, lysine, histidine, or nithine and the like; and examples of the alkanolamine for the alkanolamino group as X include triethanolamine, diethanolamine, monoethanolamine and the like.

Among the phosphate esters and the salts thereof represented by the formula (1), particularly preferred are phosphate monoesters each of which has a dodecyl group or a linear or branched alkyl group having 8 to 15 carbon atoms; and their sodium, potassium or triethanolamine salts.

The component (A) can be an a mixture of one or more of phosphate monoesters or diesters, or salts thereof, all of which are represented by the formula (1) In the case of a mixture of a phosphate monoester and a phosphate diester, the phosphate monoester preferably amounts to at least 65 wt. % of the mixture.

From the standpoint of foaming properties, the component (A) may be added in a proportion of from 2 to 60wt. %, preferably from 5 to 40 wt. %, more preferably from 10 to 35 wt. %, most preferably from 10 to 30 wt. % based on the whole composition.

The term "glyceryl ether" as the component (B) means glyceryl mono-, di- or tri-alkyl or alkenyl ether. Usually, themono-ordi-alkyl or alkenyl ether is used, with themonoether being particularly preferred. The alkyl or alkenyl group is a linear or branched alkyl or alkenyl group having 4 to 12 carbon atoms, preferably a linear or branched alkyl group having 4 to 12 carbon atoms. For example, n-butyl, isobutyl, tert-butyl, n-pentyl, isopentyl, n-hexyl, isohexyl, n-heptyl, n-octyl, 2-ethylhexyl, n-nonyl, n-decyl, n-undecyl and n-lauryl can be exemplified. In particular, glyceryl mono- or di-alkyl ethers having one or two alkyl groups having 4 to 11 carbon atoms, more preferably 6 to 10 carbon atoms, particularly 8 carbon atoms ($C_8$-alkyl), specifically glyceryl mono ($C_8$-monoalkyl) ethers, for example, glyceryl n-octyl monoether and glyceryl 2-ethylhexyl monoether are preferred.

As the glyceryl ether, the component (B), one or more glyceryl ethers can be used in combination. From the standpoint of foaming properties, the glyceryl ether may be added in a proportion of from 0.1 to 30 wt. %, preferably from 0.5 to 15 wt. %, more preferably from 1 to 10 wt. %, most preferably from 1 to 5 wt. % based on the whole composition.

The detergent composition according to the present invention may preferably be formulated into an aqueous liquid form using water as a medium. Components employed in ordinary detergent compositions can also be added as needed, including, for example, humectants such as propylene glycol, glycerin, diethylene glycol monoethyl ether, sorbitol and panthenol; conditioning components such as cationic polymers, silicone compounds and derivatives thereof; pearling agents such as ethylene glycol distearate; nonionic surfactants such as polyoxyethylene alkyl ethers, alkyl polyglucosides, glycerin fatty acid esters, and poly glycerin fatty acid esters; amphoteric surfactants such as amidopropyl betaines; anionic surfactants other than the component (A); cationic surfactants such as cetyl trimethylammonium salts; colorants such as dyes and pigments; viscosity controlling agents such as methylcellulose, polyethylene glycol and ethanol; pH adjusters such as citric acid and potassium hydroxide; salts such as sodium chloride, plant extracts, preservatives, antimicrobial agents, chelating agents, vitamins, anti-inflammatories, anti-dandruff agents, perfumes, color additives, UV absorbers, antioxidants, and cooling agents.

The detergent composition according to the present invention can be produced by a conventional method.

The detergent composition according to the present invention may be adjusted preferably to pH 5 to 10, especially to pH 5.5 to 7.

EXAMPLES

Example 1

Detergent compositions of the formulations shown in Table 1 were produced by a conventional method and were evaluated with respect to foamability and irritation. The results are also presented in Table 1.

(Evaluation Methods)

(1) Foamability

A 20-fold aqueous dilution of a detergent composition was prepared, and 100 mL (solution temperature: 40° C.) of the solution were poured in to a 100mL graduated cylinder. A 4-blade stirrer of 5 cm in diameter was then placed in the solution. The volume (mL) of foam which had generated subsequent to stirring at 1,000 r/min for 30 seconds was measured, and the foam volume was ranked in accordance with the following standard. Incidentally, the stirrer was reversed at every five seconds.

A: 200 mL≦foam volume

B: 150 mL≦foam volume<200 mL

C: foam volume<150 mL (2) Irritation

A 5-fold aqueous dilution of a detergent composition was prepared, and 10 mL aliquots of the aqueous solution were placed in glass cups of 3.5 cm in diameter attached to the forearms of 10 expert panelists and were kept in contact with their skins for 30 minutes a day. After the test was conducted for three successive days, the condition of each skin was ranked in accordance with the following standard.

A: Desquamation was observed on not more than 5 panelists.

B: Desquamation was observed on 6 or more panelists, but no erythema was observed.

C: Desquamation and erythema were observed on 6 or more panelists.

TABLE 1

| Component (wt. %) | Invention product | | Comparative product | |
|---|---|---|---|---|
| | 1 | 2 | 1 | 2 |
| Potassium salt of a phosphate ester (A)*1 | 20 | | | 20 |
| Triethanolamine salt of a phosphate ester (B)*2 | | 20 | | |
| Sodium polyoxyethylene (3) lauryl ether sulfate | | | 20 | |
| n-Octyl glyceryl ether | 3 | 3 | 3 | |
| Purified water | Balance | Balance | Balance | Balance |
| Foamability | A | A | A | C |
| Irritation | A | A | B | A |

(A)*1: A phosphate ester produced using "DIADOL 115L" (product of Mitsubishi Chemical Corporation) as a feed alcohol [a 47:31:22 (by weight) mixture of three phosphate esters $P_{11}$, $P_{13}$ and $P_{15}$ of the formula (1) in which m = 0, $R^2$ = H, and $R^1$ = $C_{11}$-, $C_{13}$-, $C_{15}$-(methyl-branched) alkyl groups, respectively]
(B)*2: A phosphate ester produced using lauryl alcohol as a feed alcohol (in the formula (1), $R^1$ = $C_{12}$-linear alkyl, m = 0, and $R^2$ = H)

Example 2

A body wash of the following formulation was produced by a conventional method.

The thus-obtained body wash was excellent in foamability and low in irritation.

TABLE 2

| (Components) | (wt. %) |
|---|---|
| Potassium salt of the phosphate ester (A)*1 | 15 |
| Lauric acid amidopropyl betaine solution (30%) | 10 |
| Lauryldiethanolamide | 2 |
| n-Octyl glyceryl ether | 2 |
| Perfume | 0.5 |
| Purified water | Balance |

[(A)*1 is as defined above.]

Example 3

A facial wash of the following formulation was produced by a conventional method.

The thus-obtained facial wash was excellent in foamability and low in irritation.

TABLE 3

| (Components) | (wt. %) |
| --- | --- |
| Potassium salt of the phosphate ester (A)*[1] | 30 |
| n-Octyl glyceryl ether | 2 |
| Glycerin | 20 |
| Perfume | 0.3 |
| Purified water | Balance |

[(A)*[1] is as defined above.]

Example 4

A facial wash of the following formulation was produced by a conventional method.

The thus-obtained facial wash was excellent in foamability and low in irritation.

TABLE 4

| (Components) | (wt. %) |
| --- | --- |
| Sodium salt of the phosphate ester (A)*[1] | 30 |
| Lauric acid amidopropyl betaine solution (30%) | 8 |
| n-Octyl glyceryl ether | 1 |
| Aqueous sorbitol solution (60%) | 25 |
| Perfume | 0.3 |
| Purified water | Balance |

[(A)*[1] is as defined above.]

Example 5

A body wash of the following formulation was produced by a conventional method.

The thus-obtained body wash was excellent in foamability and low in irritation.

TABLE 5

| (Components) | (wt. %) |
| --- | --- |
| potassium salt of the phosphate ester (A)*[1] | 10 |
| 2-Ethylhexyl glyceryl ether | 2 |
| Glyceryl monolaurate | 2 |
| Perfume | 0.3 |
| Purified water | Balance |

[(A)*[1] is as defined above.]

INDUSTRIAL APPLICABILITY

Detergent compositions according to the present invention are low in skin irritation and good in foarmability. Therefore, the detergent compositions of the present invention can be formulated, for example, as detergents for personal washing such as shampoos, body washes, facial washes and hand washes.

The invention claimed is:

1. A method for enhancing foamability which comprises adding (B) at least one glyceryl mono-alkyl ether having an alkyl group of 6 to 10 carbon atoms to a detergent composition for personal washing comprising (A) at least one phosphate ester or a salt thereof represented by the following formula (1):

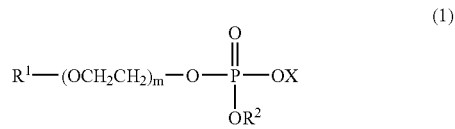

wherein $R^1$ represents a linear or branched hydrocarbon group having 11 to 18 carbon atoms, m stands for a number of from 0 to 3 on weight average, X represents a hydrogen atom, an alkali metal atom, ammonium, a basic amino acid residual group, or an alkanolamino group having a hydroxyalkyl group of 2 to 3 carbon atoms, and $R^2$ represents $-(CH_2CH_2O)_m-R^1$ or X, or a mixture thereof, wherein foamability is at least 150 mL of foam from 100 mL of a 20-fold aqueous dilution of said detergent composition.

2. The method according to claim 1, wherein said component (B), is a linear or branched alkyl monoether.

3. The method according to claim 1, wherein the monoester in said phosphate ester as the component (A) amounts to at least 65 wt.% based on a total amount of the monoester and diester.

4. The method according to claim 1, wherein in said phosphate ester as the component (A), $R^1$ in the formula (1) is a linear or branched hydrocarbon group having 11 to 15 carbon atoms.

5. The method according to claim 1, wherein the phosphate ester as the component (A) is a phosphate ester having an α-branched alkyl group.

6. The method according to claim 1, wherein the content of said component (B) is from 0.1 to 30 wt. % based on the whole composition.

7. The method according to claim 1, wherein the detergent composition is a body wash.

8. The method according to claim 1, wherein the detergent composition is a facial wash.

9. A method for washing a person, which comprises:

applying to a person a detergent composition comprising (A) at least one phosphate ester or a salt thereof represented by the following formula (1):

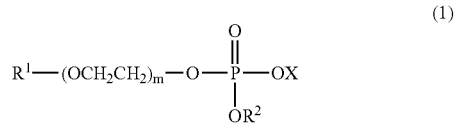

wherein $R^1$ represents a linear or branched hydrocarbon group having 11 to 18 carbon atoms, m stands for a number of from 0 to 3 on weight average, X represents a hydrogen atom, an alkali metal atom, ammonium, a basic amino acid residual group, or an alkanolamino group having a hydroxyalkyl group of 2 to 3 carbon atoms, and $R^2$ represents $-(CH_2CH_2O)_m-R^1$ or X, or a mixture thereof, and (B) at least one glyceryl mono-alkyl ether having a alkyl group of 6 to 10 carbon atoms wherein said detergent composition has foamability of at least 150 mL of foam from 100 mL of a 20-fold aqueous dilution of said detergent composition.

10. The method according to claim 9, wherein said component (B), is a linear or branched alkyl monoether.

11. The method according to 9, wherein the monoester in said phosphate ester as the component (A) amounts to at least 65 wt. % based on a total amount of the monoester and diester.

12. The method according to 9, wherein in said phosphate ester as the component (A), $R^1$ in the formula (1) is a linear or branched hydrocarbon group having 11 to 15 carbon atoms.

13. The method according to 9, wherein the phosphate ester as the component (A) is a phosphate ester having an α-branched alkyl group.

14. The method according to 9, wherein the content of said component (B) is from 0.1 to 30 wt. % based on the whole composition.

15. The method according to claim 9, wherein the detergent composition is a body wash.

16. The method according to claim 9, wherein the detergent composition is a facial wash.

17. The method according to claim 1, wherein said component (B), is a mono-elkyl ether having 8 carbon atoms.

18. The method according to claim 9, wherein said component (B), is a mono-elkyl ether having 8 carbon atoms.

* * * * *

UNITED STATES PATENT AND TRADEMARK OFFICE
CERTIFICATE OF CORRECTION

| | | |
|---|---|---|
| PATENT NO. | : 7,504,370 B2 | Page 1 of 1 |
| APPLICATION NO. | : 10/969842 | |
| DATED | : March 17, 2009 | |
| INVENTOR(S) | : Matsumoto et al. | |

It is certified that error appears in the above-identified patent and that said Letters Patent is hereby corrected as shown below:

On the title page, the Terminal Disclaimer information has been omitted. Item (45) and the Notice information should read as follows:

Item --(45) **Date of the Patent: * Mar. 17, 2009**

(*) Notice: Subject to any disclaimer, the term of this patent is extended or adjustment under 35 U.S.C. 154(b) by 0 days.

This patent is subject to a terminal disclaimer.--

Signed and Sealed this

Twenty-fifth Day of May, 2010

David J. Kappos
*Director of the United States Patent and Trademark Office*